US006859657B1

(12) United States Patent
Barnard

(10) Patent No.: US 6,859,657 B1
(45) Date of Patent: Feb. 22, 2005

(54) PERSONAL COMMUNICATIONS APPARATUS

(75) Inventor: Michael E. Barnard, Redhill (GB)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/379,955

(22) Filed: Aug. 24, 1999

(30) Foreign Application Priority Data

Aug. 29, 1998 (GB) .............................................. 9818840

(51) Int. Cl.[7] .............................................. H04M 1/00
(52) U.S. Cl. ................ 455/575.6; 455/41.1; 455/343.1; 455/348
(58) Field of Search ................................ 455/567, 557, 455/575, 347, 90, 525, 456.1–456.6, 344, 575.1–575.7, 90.1, 41.2, 41.1, 41.3, 523, 550.1, 556.1, 575.6, 343.1, 348; 379/430, 433

(56) References Cited

U.S. PATENT DOCUMENTS

| | | | | |
|---|---|---|---|---|
| 5,239,521 A | * | 8/1993 | Blonder ........................ | 368/10 |
| 5,381,387 A | * | 1/1995 | Blonder et al. ............... | 368/10 |
| 5,467,324 A | * | 11/1995 | Houlihan ...................... | 368/10 |
| 5,499,292 A | * | 3/1996 | Blonder et al. .............. | 379/433 |
| 5,564,082 A | * | 10/1996 | Blonder et al. ............... | 455/90 |
| 5,659,611 A | * | 8/1997 | Saksa ........................... | 379/433 |
| 5,873,041 A | * | 2/1999 | Ishii ............................ | 455/457 |
| 6,218,958 B1 | * | 4/2001 | Eichstaedt et al. ..... | 340/825.46 |
| 6,223,018 B1 | * | 4/2001 | Fukumoto et al. ............. | 455/4 |
| 6,272,359 B1 | * | 8/2001 | Kivela et al. ................ | 455/567 |

FOREIGN PATENT DOCUMENTS

WO          WO9827702         6/1998

OTHER PUBLICATIONS

By M. Fukumoto & Y. Tonomura, "Body Coupled Fingering: Wireless Wearable Keybord", Published Papers ACM Conference on Human Factors in Computing Systems (CHI 97), Mar. 22–27, 1997, Altlanta, USA, pp. 147–154.
By E. Post et al. " Intrabody Buses for Data and Power", Pub. Papers of the First International Symposium on Wareable Computers, Oct. 13–14, 1997, Cambridge, USA, pp. 52–55.
By Rukumoto M. et al.: "Body Coupled Fingering: Wireless Wearable Keyboard"; Conference on Human Factors in Computing Systems, US, NY, ACM, 1997, pp 147–154.

* cited by examiner

*Primary Examiner*—Charles Craver
(74) *Attorney, Agent, or Firm*—Jack D. Slobod

(57) ABSTRACT

A personal communications apparatus comprises a first part, having a microphone (114), and a second part, having a loudspeaker (118). The first part is adapted to be worn on a user's wrist (202) and the second part is adapted to be worn on their finger. In use, the user's hand is held up to the side of their head, thereby placing the microphone (114) adjacent to their mouth and the loudspeaker (118) adjacent to their ear. Communication between first and second parts of the apparatus is by means of signals transmitted via the user's skin.

In a non-illustrated embodiment the second part is adapted to be worn on the ear.

15 Claims, 3 Drawing Sheets

PERSONAL COMMUNICATIONS APPARATUS

The present invention relates to a personal communications apparatus comprising a first part having a microphone and a second part having an loudspeaker. In particular, such an apparatus may be a wireless telephone or two-way radio transceiver.

At present, wireless telephones are available either with microphones and loudspeakers built into the main body of the phone, which is then hand-held in a conventional manner, or with headsets which enable the user to operate in a hands-free manner. Progress in miniaturization of electronic components has enabled proposals for wrist-carried wireless telephones, which have the advantage of being more convenient to carry than a separate hand-held telephone. However, such proposals must address the problem of extending the distance between the microphone and loudspeaker to correspond to the actual spacing between a user's mouth and ear.

A range of solutions to this problem has been suggested. Those discussed below all relate to a wrist-carried radio telephone having a case including a transceiver, and a strap for attaching the case to the user's wrist.

U.S. Pat. No. 5,659,611 discloses a telephone in which a microphone and an earpiece are mounted in separate caps which, when in use, are placed on two of the user's fingertips. Electrical connections between the transceiver in the wrist-mounted case and the microphone and earpiece are provided by electrical wires. When not in use the electrical connection wires retract into the case and the caps are stored in close proximity to the case.

In the telephone disclosed in U.S. Pat. No. 5,467,324 a microphone is included in the case, while a loudspeaker can be pulled out from the case on a flexible tether member. The length of the flexible tether is sufficient to permit the loudspeaker to be placed near the user's ear while the user holds their wrist so that the microphone, on the case of the apparatus, is adjacent to the user's mouth.

U.S. Pat. No. 5,239,521 discloses a telephone where the strap has a top layer and a bottom layer. The top layer of the strap is releasable in the area where the case and strap meet and is connected to the bottom layer of the strap by a pivotable hinge which permits the top layer to rotate laterally of the strap. A loudspeaker is located on the free end of the released top layer, while a microphone is located on the strap. In use, the top layer is released and rotated to position the speaker in the palm of the user's hand. The hand is then raised to the side of the user's head to enable a private telephone conversation to be made.

A disadvantage of all of these proposals is that they are cumbersome, involving either mechanically vulnerable extensions or unsightly wires.

An object of the present invention is to provide a personal communications apparatus having an adequate separation between microphone and loudspeaker without requiring mechanically vulnerable extensions or unsightly wires.

According to the present invention there is provided a personal communications apparatus comprising a first part having a microphone and a second part having an loudspeaker, characterised in that communication between said first and second parts is by means of signals transmitted via the skin of the user.

The present invention is based upon the recognition, not present in the prior art, that the required physical separation between microphone and loudspeaker can be achieved by transmitting data and power via the skin of the user.

The use of body coupling for communication between a transmitter mounted on a finger and a receiver mounted on the wrist of the same hand is discussed in the paper "Body Coupled FingeRing: Wireless Wearable Keyboard" by M Fukumoto and Y Tonomura in the published papers of the ACM Conference on Human Factors in Computing Systems (CHI 97), 22–27 March 1997, Atlanta, USA, pp. 147–154. The application being considered in this paper is an input device for a computer that utilises a typing action without requiring a bulky keyboard.

The possibilities for wireless transmission of data and power around the body are discussed in the paper "Intrabody Buses for Data and Power" by E Post et al in the published papers of the First International Symposium on Wearable Computers, 13–14 October 1997, Cambridge, USA, pp. 52–55. Such Personal Area Networks (PANs) have been demonstrated with data rates of 9600 bits per second (bps), with the possibility of data rates of 50,000 bps in the near future. Wireless transmission of 20 mW of power from a hand to a foot has also been demonstrated, extracted from a 200 mW signal at 1 MHz.

Embodiments of the present invention will now be described, by way of example, with reference to the accompanying drawings, wherein.

In the drawings the same reference numerals have been used to indicate corresponding features.

Figure 1:
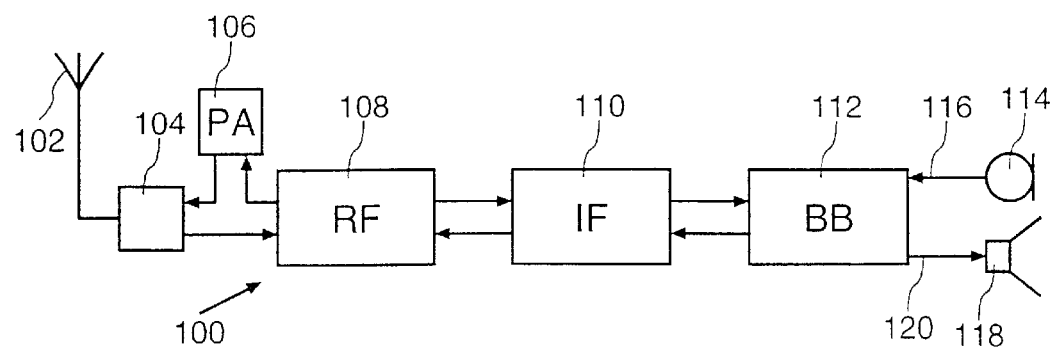
FIG. 1 is a block schematic diagram of a personal communications apparatus.

A block schematic diagram of a personal communications apparatus 100 is shown in FIG. 1. This particular example is based on a GSM cellular telephone, but similar principles apply to other cellular telephony standards and to other personal communications apparatus, for example two-way radio.

Consider first the receiver part of the circuitry operating on a voice telephone call. An antenna 102 receives signals from a remote base station, which signals pass through a diplexer filter 104, the purpose of which is to prevent strong transmitted signals from leaking into and overloading receiver circuitry. The signals then pass into an radio frequency transceiver block (RF) 108, which down-converts the RF signal to a lower intermediate frequency (IF).

The IF signals pass to an intermediate frequency block (IF) 110 which down-converts the IF signal to a baseband signal. This signal then passes to a baseband processing block (BB) 112. This block performs a variety of tasks, including speech decoding, channel decoding and deinterleaving. Received audio signals are converted back to analogue signals for reproduction on a loudspeaker 118 or other suitable output device.

Now consider the transmission side of the circuitry. Voice signals are received by a microphone 114, or other suitable input device, and passed to the baseband processing block 112, where they are converted to digital form. The baseband processing block 112 then encodes the speech and performs channel coding and interleaving to reduce the received bit error rate. The resultant signal for transmission is modulated and passed to the IF block 110. Here the baseband signals are transposed up to an IF frequency.

The IF signal is passed to the RF transceiver block 108 where it is mixed up to the RF transmission frequency and amplified to the required power by a power amplifier (PA) 106. It is then passed through the diplexer filter 104 and transmitted by the antenna 102.

In prior art personal communications apparatus signal paths 116 and 120, from the microphone 114 to the baseband processing block 112 and from the baseband processing block 112 to the loudspeaker 118 respectively, are provided by conducting wires. In an apparatus made in accordance with the present invention at least one of the signal paths 116, 120 is via a user's skin.

Figure 2:
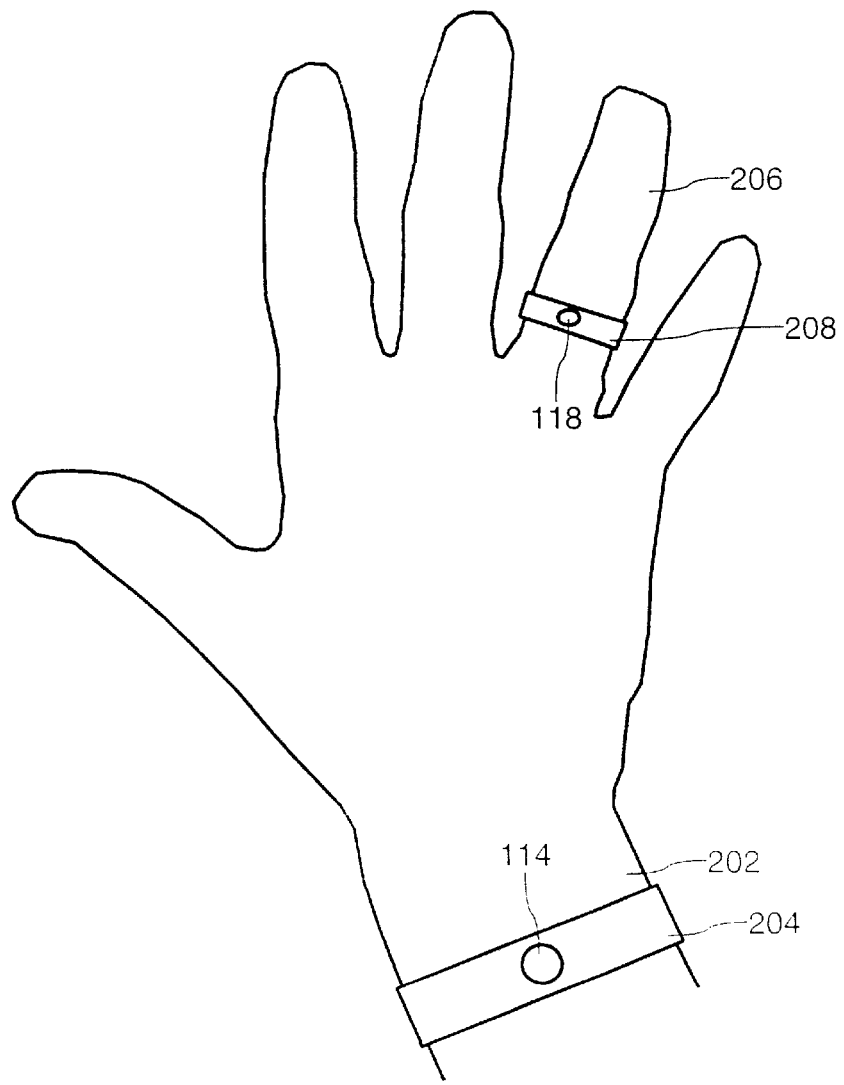
FIG. 2 is a view of a personal communications apparatus made in accordance with the present invention.

An embodiment of a personal communications apparatus 100 made in accordance with the present invention is shown in FIG. 2. A microphone 114 is mounted on the inside of a wrist 202 of a user by means of a strap 204. More particularly, the microphone 114 is mounted directly on the strap 204, which strap provides the signal path 116 between the microphone 114 and the baseband processing block 112 which is housed in a casing 302 (FIG. 3) on the outside of the user's wrist 202. Also housed in this casing is the remainder of the circuitry of the personal communications apparatus 100 with the exception of a loudspeaker 118 (and its associated drive circuitry).

The loudspeaker 118 is mounted on a finger 206 of the user by means of a ring 208. The signal path 120 between the loudspeaker 118 and baseband processing block 112 is via the skin of the user, taking advantage of its electrical properties.

Figure 3:
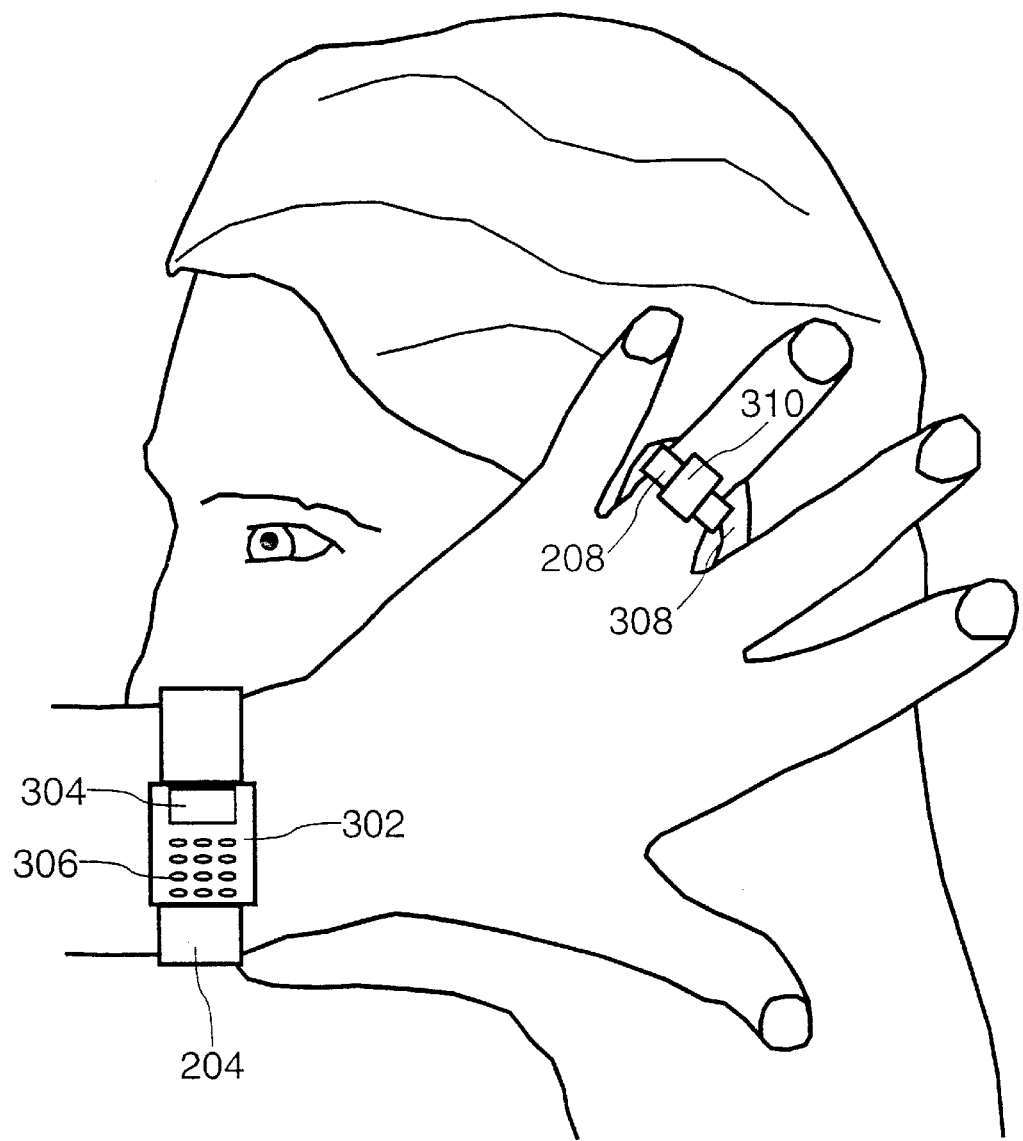
FIG. 3 is a view of a personal communications apparatus made in accordance with the present invention being used as a telephone.

A view of the personal communications apparatus 100 in use is shown in FIG. 3. The user's hand is held against the side of their head so that the ring 208 is adjacent to an ear 308, thereby enabling sounds from the loudspeaker 118 (FIG. 2) to be heard with minimal external interference, and so that the strap 204 is adjacent to the mouth, thereby enabling the microphone 114 (FIG. 2) to pick up spoken sounds. This required position is a fairly natural pose, so use of the personal communications apparatus 100 is comfortable and convenient.

A casing 302 is attached to the strap 204, and includes the majority of the circuitry for the personal communications apparatus 100. Also provided is a display 304 and a keyboard 306 for controlling the apparatus 100. An antenna (not shown) is provided in the strap 204 or in the casing 302. The ring 208 also carries a casing 310 containing circuitry (not illustrated) to receive signals from which an audio signal can be extracted and provided to the loudspeaker 118 for reproduction.

Other variations on the above arrangement will be apparent to those skilled in the art. Examples of such variations include, but are not limited to:

The microphone 114 could be made integral with the casing 302 which would then be worn on the inside of the user's wrist 202.

The casing 302 could be located elsewhere on the user's body, communicating with both the loudspeaker 118 and microphone 114 by means of signals transmitted via the skin of the user.

The loudspeaker 118 could be mounted elsewhere on the user's body. For example, the ring 208 could be replaced by an earpiece containing the loudspeaker.

The keyboard 306 could be replaced by a voice recognition device (not shown).

Timekeeping circuitry (not shown) could be included in the casing 302, enabling the apparatus 100 to function as a watch or alarm.

Figure 4:
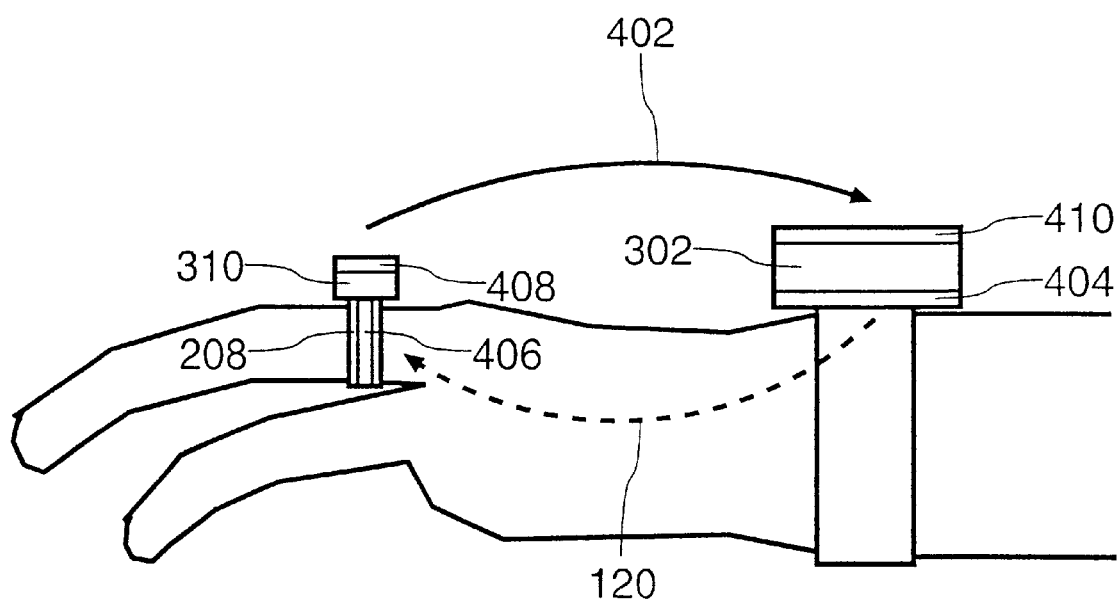
FIG. 4 is a diagram illustrating a means of electrical connection between finger-mounted loudspeaker and the remainder of a personal communications apparatus.

An example of one possible arrangement for maintaining an electrical connection between the loudspeaker 118 and baseband processing block 112 is shown in FIG. 4. In order to create an electrical circuit through which suitable signals can be transmitted, a signal path 120 from the wrist casing 302 to the ring casing 310 and a return path 402 from the ring casing 310 to the wrist casing 302 are required. Power to drive the circuitry in the ring casing 310 is extracted from the received signal.

In the illustrated embodiment the signal path 120 is via the user's skin. A 100 kHz sine wave is injected into the skin at the user's wrist 202 via a capacitively-coupled electrode 404. The signal is received by an electrode 406 built into the ring 208. The return path 402 is directly coupled via air, the signal being transmitted from an electrode 408 on the ring casing 310 and received by an electrode 410 on the wrist casing 302.

From reading the present disclosure, other modifications will be apparent to persons skilled in the art. Such modifications may involve other features which are already known in the design, manufacture and use of personal communications apparatus and component parts thereof, and which may be used instead of or in addition to features already described herein.

In the present specification and claims the word "a" or "an" preceding an element does not exclude the presence of a plurality of such elements. Further, the word "comprising" does not exclude the presence of other elements or steps than those listed.

What is claimed is:

1. A personal communications apparatus comprising:
   a first part comprising, co-disposed in a single physically distinct unit,
      a microphone;
      a strap for attachment to a wrist; and
   a second part comprising, co-disposed in a single physically distinct unit,
      means for attaching to a user body part other than the wrist;
      a loudspeaker; and
      means for communicating with said first part using signals transmitted via the skin of the user, wherein the second part has means for deriving its power from the signals transmitted by the first part.

2. An apparatus as claimed in claim 1, characterized in the first part further comprises a case incorporating a transceiver and baseband processing circuitry.

3. An apparatus as claimed in claim 1, characterized in that the second part is adapted to be carried by a finger.

4. An apparatus as claimed in claim 3, characterized in that the second part includes an electrode for receiving signals from the user's skin.

5. An apparatus as claimed in claim 3, wherein the second part is affixed to a finger ring.

6. An apparatus as claimed in claim 1, characterized in that the second part is adapted to be worn as an earpiece.

7. An apparatus as claimed in claim 6, characterized in the first part further comprises a case incorporating a transceiver and baseband processing circuitry.

8. An apparatus as claimed in claim 6, characterized in that the second part includes an electrode for receiving signals from the user's skin.

9. An apparatus as claimed in claim 8, characterized in that the second part comprises means for deriving power from the signals from the user's skin.

10. The apparatus of claim 1, wherein the microphone is mounted on the strap.

11. An apparatus for personal communications comprising:

a first pad comprising:
  a microphone;
  means for communicating via a user's skin;
a second part comprising:
  a loudspeaker;
  means for communicating with the first part via the user's skin; and
  means for deriving power for operation of the second part from signals received from the first part via the user's skin.

12. The apparatus of claim 11, further comprising a strap for attaching to the user's wrist, wherein the microphone is mounted on the strap.

13. Personal communications device comprising:
means for communicating with a user's ear comprising:
  a finger ring; and
  at least one unit mechanically integrated with the finger ring comprising:
    means for receiving input signals via the user's skin; and
    means for providing audible signals derived from the input signals to the user's car, wherein the means for providing audible signals further comprises means for driving power from received input signals; and
a base station unit comprising:
  a wrist strap;
  at last one unit mechanically integrated with the wrist strap, including:
    transceiver means for communicating with at least one external device;
    means for receiving audible signals from the user's mouth and providing them to the transceiver means for transmission to the external device; and
    means for communicating signals from the external device via the skin to the means for communicating with the user's car.

14. The device of claim 13, wherein the unit mechanically integrated with the wrist strap further comprises:
  display means for communicating visual information to the user; and
  means for receiving numeric input from the user for specifying how to locate the external device.

15. A communication device comprising:
a sound producing unit, comprising:
  a finger ring;
  at least one unit integrated with the finger ring comprising:
    means for receiving input signals; and
    means for providing audible signals derived from the input signals to user's ear, wherein the means for providing audible signals further comprises means for deriving power from received input signals; and
a base station comprising:
  a wrist strap;
  at least one unit integrated with the wrist strap, including:
    transceiver means for communicating with at least one external device;
    means for receiving audible signals from the user's mouth and providing them to the transceiver means for transmission to the external device; and
    means for transmitting signals from the external device to the sound producing unit.

* * * * *